United States Patent [19]

Suovaniemi et al.

[11] 4,259,290
[45] Mar. 31, 1981

[54] TRANSFER DEVICE FOR ANALYSIS EQUIPMENT

[75] Inventors: Osmo A. Suovaniemi; Pertti Ekholm, both of Helsinki; Esko Kaukanen, Espoo, all of Finland

[73] Assignee: Kommandiittiyhtio Finnpipette Osmo A. Suovaniemi, Helsinki, Finland

[21] Appl. No.: 49,161

[22] Filed: Jun. 18, 1979

[30] Foreign Application Priority Data

Jul. 5, 1978 [FI] Finland ................... 782159

[51] Int. Cl.³ ................ G01N 21/00; B65G 43/00
[52] U.S. Cl. ............................... 422/65; 422/67; 422/100; 73/423 A; 198/341
[58] Field of Search .................. 422/65, 67, 100; 141/129, 130, 185; 414/750; 73/423 A; 356/244; 198/472, 341

[56] References Cited

U.S. PATENT DOCUMENTS

| | | | |
|---|---|---|---|
| 3,666,076 | 5/1972 | Miller et al. | 198/472 |
| 3,708,264 | 1/1973 | Jottier | 422/65 |
| 3,802,782 | 4/1974 | Natelson | 422/65 |

FOREIGN PATENT DOCUMENTS

| | | |
|---|---|---|
| 1,572,219 | 6/1969 | France . |
| 2,117,393 | 7/1972 | France . |
| 1,265,230 | 3/1972 | United Kingdom ............ 141/130 |

*Primary Examiner*—William F. Smith
*Assistant Examiner*—Chris Konkol
*Attorney, Agent, or Firm*—Hopgood, Calimafde, Kalil, Blaustein & Lieberman

[57] ABSTRACT

The subject of the present invention is a transfer device for analysis equipment, which transfer device comprises a track consisting of, inter alia, guide and support rails on which to transfer a pit plate on a transport cassette along the track. The transport cassette includes a traction rail parallel to the guide and support rails. Traction units are fitted onto the track in the transfer device as means operative jointly with said traction rail to move the transport cassette. In order to control the operation of the traction units, the traction rail is provided with sign codes readable by means of an optical reading device. This indicates the position of the cassette relative to the optical reading device so that the transport cassette may be stopped to position the desired line of pits, transverse to the track for operations to be performed in the analysis equipment, such as liquid dosage, photometric measurement operations, etc.

8 Claims, 2 Drawing Figures

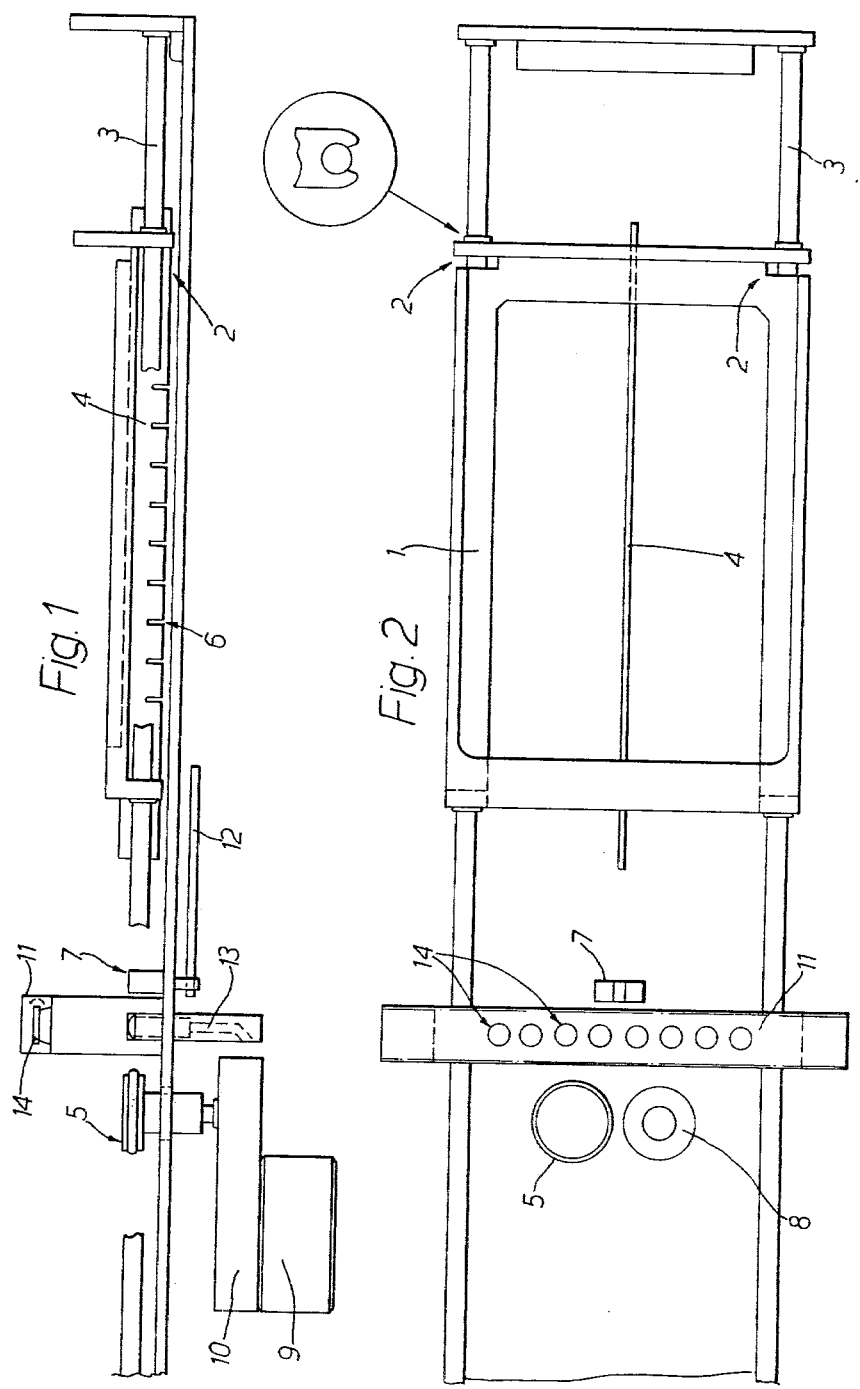

TRANSFER DEVICE FOR ANALYSIS EQUIPMENT

The subject of the present invention is directed to a transfer device for use in analysis equipment. More particularly, it relates to a transfer device comprising a track on which to transfer a pit plate on the transport cassette.

An objective is to provide analysis equipment with a transfer system which is sufficiently precise to transfer pit plates (microtiter plates, such as those manufactured by Cooke, Linbro, Titertek), measurement cuvettes, measurement cuvette sets (such as the Finnpipette cuvette set), dosage vessels, or their equivalents, in analysis equipment having photometric measurement devices, liquid dosage devices, etc. or combinations of such devices. In particular, photometric devices require precise positioning, both in the transverse direction and in the direction of movement. The system to be described now is suitable both for multi-channel systems wherein a row of samples is measured at the same time and for single-channel systems. It is also suitable for vertical or horizontal beam spectrophotometric measurement.

The transfer device in accordance with the present invention is mainly characterized in that the transport cassette (1) includes a traction rail (4) parallel to the track, traction units being fitted onto the track in the transfer device as means operative jointly with said traction rail, said traction units consisting, for example, of a friction wheel (5) or friction wheels driven by a linear motor or equivalent, and possibly a counter-wheel (8) counter-wheels. In order to control the operation of the traction units, the traction rail (4) is provided with sign codes (6), such as holes, transverse grooves, or their equivalent, readable by means of an optical reading device (7), so as to indicate the position of the cassette relative to the optical reading device (7). Thus, the transport cassette (1) may be stopped so as to guide the desired line of pits, transverse to the track, exactly in the way required by the operations to be performed in the analysis equipment, such as liquid dosage, photometric measurement operations, etc.

The device in accordance with the present invention involves, for example, the following advantages:

The cassettes may be detachable from the track.

The transport cassette is supported on the guide and support rails by several points, whereby good mechanical rigidity is achieved.

The length of the track may be arbitrary.

The cassette may be of a type passing through and/or it may be returned.

The same system may include several cassettes.

The movement can be made constant, and it may take place in both directions.

In long systems (such as where there is a combination of several devices each of which includes a positioning mechanism), instead of precise transfer mechanisms such as the traction rail, it is possible to make use of spring force, gravity, etc. in order to produce intermediate movements.

In long systems, cassettes may also be connected to each other as a train. At the beginning or end of the train there may be a locomotive including a transfer motor which is moved by traction against the support rails by means of friction wheels or equivalent. The locomotive may either operate as a precise transfer mechanism or as only an auxiliary means to produce intermediate transfers.

Along the track, there may be pipetting, thermostating, shaking, measurement, etc. stations.

In the thermostating and locomotive cases, the support rails may also function as suppliers of electricity to the motor and to the thermostat.

The invention may be better understood from the following description read in conjunction with the attached drawing, wherein:

FIG. 1 shows a side view of a transfer device in accordance with the present invention, and FIG. 2 shows the transfer device of FIG. 1 as viewed from above.

The transfer device shown in FIGS. 1 and 2 comprises a track consisting of guide and support rails 3 for the purpose of transferring a pit plate (not shown) on the transport cassette 1 along the track. The transport cassette is supported on rails 3 by supports 2 as shown enlarged in the detail of FIG. 2. Typically, the four corners are unsupported. The transport cassette 1 includes a traction rail 4 parallel to the track, illustratively, positioned in the center of the cassette. A friction wheel 5, driven by a linear motor 9 or equivalent, and a counter-wheel 8 to the friction wheel 5 are fitted as traction units onto the track in the transfer device and constitute means operating jointly with the traction rail 4 to transfer the cassette. In order to control the operation of the traction unit 5 and 8, the traction rail 4 is provided with sign codes 6, such as holes, transverse grooves, or equivalent, readable by means of an optical reading device 7, so as to indicate the position, in relation to the optical reading device 7, at which the transport cassette 1 is located so that it may be stopped in the desired position.

In the embodiment shown in FIGS. 1 and 2 it is seen that the traction rail 4 of the transport cassette 1 first passes by an optical reader 7. The sign codes 6 in the traction rail 4—in the present case rectangular slits allowing the signal to pass through—indicate when transport cassette 1 is in the position at which transport cassette 1 must stop. The optical reader 7 and the motor 9 are by means of input/output interface electronics 12 connected to the electronics of the operation at each particular point of concern.

The motor 9 operates by means of a control system at each work station and, by the intermediate of a transmission system 10, rotates the friction wheel 5. Opposed to the friction wheel 5, there is a counter-wheel 8, against which the traction rail 4 is pressed by the effect of the friction wheel 5. The traction surface of the friction wheel 5 may be resilient, or the friction wheel 5 with its mechanism of rotation may also be provided with a spring load against the counter-wheel 8. Alternatively, the friction wheel 5 may be mounted rigidly and the counter-wheel 8 may be provided with a spring load in a way suitable for the purpose.

Thus, the movement of the transport cassette 1 takes place so that the traction rail 4 is fixed, e.g., around the middle of the cassette 1, to which rail 4 it is possible to direct the transfer force, e.g., by means of one or several friction wheels 5, counter-rolls 8, and linear motor or equivalent. The same rail 4 may also function as a synchronization rail for the stopping system. A sign code 6, holes or equivalent, in the rail 4 may be read by means of an optical reader 7, whereby the positioning can be made precise. The code may also contain more information than what is required for precise stopping alone.

The embodiment of transfer system shown in FIGS. 1 and 2 is provided with a measurement head 11, which illustratively is a multi-channel vertical beam spectrophotometer. Several optical conductors 13 are placed in a line, which conductors transmit measurement beams, and at corresponding positions there are detectors 14 that receive the measurement beams.

The analysis equipment may have provisions for measurement techniques based on, e.g., weight analysis and isotope measurement, photometry, spectrophotometry, fluorometry, or turbidometry.

The overall system in which the present invention is useful may comprise a current source, a light source, an optical instrument system, amplifiers and transformers suitable for the purpose, electronics controlling the entire system or parts of same (e.g., micro-processors or an external control system), and output systems, which may be connected to other functions related to the overall system. Into the cassette 1, it is possible to place, for example, a microtiter plate which comprises twelve successive lines, each consisting of eight separate pits. The measurement beam passes from the conductor 13, through a solution in the pit, to the detector 14. The measurement of the pits in one line may take place at the same time as in the multi-channel device of FIG. 2 or one pit at a time. After measurement, the cassette 1 is automatically shifted so that the next line of pits comes for the measurement position. The correct positions of the lines of pits are determined by the sign codes 6 in the traction rail. The above transfer and measurement system may have provision for other functions, such as liquid dosage (pipetting and/or diluting), thermostating of the entire transport cassette 1 or of the microtiter plate placed in same, etc. The measurement of the pits in the microtiter plate can be performed once or several times by shifting the microtiter plate or by returning the pit or pits concerned for repeated measurement.

The timing and controlling of the other functions related to the transfer system may be handled centrally by means of electronics (e.g., microprocessors) included in the system and/or placed outside the system. The transfer system described here may also move as an entire unit certain distances in appropriate directions. This movement of the entire system may be connected with systems of the types described above, such as measurement, liquid dosage, diluting, and thermostating.

What we claim is:

1. A transfer device for analysis equipment of the type wherein said transfer device comprises a track consisting of guide and support rails (3) on which to transfer a pit plate on a transport cassette (1) along the track, characterized in that the transport cassette (1) includes a traction rail (4) parallel to said guide and support rails, traction units are fitted onto the track in the transfer device as means operative jointly with said traction rail, said traction units consisting of at least one friction wheel (5) driven by motorized means, and an optical reader is mounted on said track so as to align with said traction rail, said traction rail (4) being provided with sign codes (6) readable by means of said optical reader (7) so as to indicate the position relative to the optical reader (7) at which the transport cassette (1) is to be stopped so as to position the desired line of pits in said cassette as required by the operations to be performed in the analysis equipment.

2. A transfer device as claimed in claim 1, characterized in that the transport cassette (1) is mounted detachably on the guide and support rails (3) of the transfer track.

3. A transfer device as claimed in claim 1, characterized in that the transport cassette (1) is slideably supported to the transfer rails (3) at four points (2).

4. A transfer device as claimed in claim 1, characterized in that the traction rail of the transport cassette (1) is arranged parallel to said guide and support rails and is fixed in the center of cassette (1).

5. A transfer device as claimed in claim 1, characterized in that the central portion of the transport cassette (1) is open over the area corresponding to the pits in a pit plate placed into the cassette and the traction rail (4) is placed between lines of pits parallel to the track.

6. A transfer device for analysis equipment, said transfer device comprising a track consisting of guide and support rails (3) on which to transfer a pit plate on a transport cassette (1) and motorized traction units (5,8) which are arranged in the track between the transport cassette (1) and the guide and support rails (3) characterized in that the central portion of the transport cassette (1) is open over the area corresponding to the pits in the pit plate and a traction rail (4) is fixed in the middle of the central portion between lines of pits and parallel to the guide and support rails, the traction rail (4) being provided with sign codes (6); and the traction units include at least one motor driven friction wheel which operates jointly with the traction rail to produce linear movement of the transport cassette, the operation of the traction units being controlled by means of an optical reader (7) arranged in the track so as to read the sign codes (6) to indicate the position of the transport cassette relative to the optical reader (7).

7. The device of claim 6 wherein said sign codes comprise transverse grooves or holes.

8. The device of claim 6 wherein said traction unit comprises a friction wheel driven by a linear motor and a counter-wheel opposed to the friction wheel.

* * * * *